United States Patent [19]

Hladky et al.

[11] Patent Number: 5,069,774
[45] Date of Patent: Dec. 3, 1991

[54] SURFACE MOUNTING CORROSION PROBE

[75] Inventors: Karel Hladky; David G. John, both of Manchester, United Kingdom

[73] Assignee: University of Manchester Institute of Science & Technology, Manchester, England

[21] Appl. No.: 469,535
[22] PCT Filed: Sep. 16, 1988
[86] PCT No.: PCT/GB88/00753
§ 371 Date: May 21, 1990
§ 102(e) Date: May 21, 1990
[87] PCT Pub. No.: WO89/02589
PCT Pub. Date: Mar. 23, 1989

[30] Foreign Application Priority Data

Sep. 19, 1987 [GB] United Kingdom ............... 87-22088

[51] Int. Cl.⁵ .............................................. G01N 17/04
[52] U.S. Cl. ................................. 204/404; 204/153.11
[58] Field of Search ........................... 204/153.11, 404; 324/71.2, 448, 700

[56] References Cited

U.S. PATENT DOCUMENTS

| 4,065,373 | 12/1977 | Martin et al. | 204/404 |
| 4,575,678 | 3/1986 | Hladky | 324/425 |
| 4,703,253 | 10/1987 | Strommen | 324/700 |
| 4,703,255 | 10/1987 | Strommen | 324/700 |
| 4,861,453 | 8/1989 | Matsuoka et al. | 204/404 |
| 4,927,503 | 5/1990 | Polly | 204/153.11 |
| 4,942,354 | 7/1990 | Miller | 324/71.2 |

FOREIGN PATENT DOCUMENTS 2335419 6/1975 Fed. Rep. of Germany ...... 204/404

Primary Examiner—Aaron Weisstuch
Attorney, Agent, or Firm—Spensley Horn Jubas & Lubitz

[57] ABSTRACT

A surface mounting corrosion probe comprising a frame adapted for securing to a surface of a reinforced concrete structure, and a resilient pad arranged such that when the frame is secured to such a structure a front surface of the pad is pressed against the structure surface. A reference electrode is located centrally relative to the front surface of the pad so as to contact the surface of any structure against which the pad is pressed. An annular portion of the front surface of the pad which extends radially outwards from the center towards adjacent the periphery of the pad is electrically conductive, and a terminal is provided which is electrically connected to that annular portion. Corrosion monitoring instruments are connected to the terminal and the reference electrode to monitor corrosion of reinforcement beneath the surface of a structure to which the frame is secured.

7 Claims, 1 Drawing Sheet

SURFACE MOUNTING CORROSION PROBE

The present invention relates to a surface mounting corrosion probe for use in monitoring the rate of corrosion of steel reinforcement embedded in concrete.

In normal circumstances steel embedded in concrete corrodes at a very low rate. This is due to the high alkalinity of the concrete environment which causes the surface of the steel to remain in an electrochemically passive state. A number of external factors may lead however to the ingress of aggressive ions, such as chloride ions, into the concrete. Degradation of the concrete may also occur as a result of the action of carbon dioxide and water present in the atmosphere. These factors can lead to an increase in the rate of corrosion of the reinforcing steel, endangering both the integrity and strength of the reinforced concrete structure. Corrosion of the steel reinforcemnt can lead to an accumulation of corrosion products which, being more voluminous than the original steel, exert pressure on the concrete covering the reinforcement, eventually leading to cracking and spalling. Loss of metal can also lead to localised thinning and weakening of the reinforcing steel, again weakening the concrete structure, necessitating expensive repairs or shortening the life of the structure.

It is desirable therefore to be able to determine non-destructively the rate of corrosion of steel reinforcement in any part of a given suspect structure, and various techniques have been developed to do this.

Electrochemical techniques have been applied to the assessment of the corrosion of reinforcing steel and rely on the measurement of the natural electrochemical potential of the reinforcing elements. Typically, a reference electrode is placed on the concrete surface of the structure and connected to the reinforcement via a voltmeter. A technique known as 'potential mapping' or 'half cell measurement' uses this approach, measuring the natural corrosion potential values over a grid of locations drawn on the surface of the structure. Subsequent analysis of the data then uses an empirical criterion to determine which parts of the embedded reinforcement are at risk from corrosion damage. This procedure is widely used and is subject to an ASTM specification (C876-80). The technique does not provide information as to the rate of corrosion attack, indicating only the likelihood of corrosion occurring.

Electrochemical techniques of 'linear polarisation resistance measurement' and 'a.c. impedance' have also been used in the past. These techniques measure the response of the electrochemical processes occurring naturally on the steel/concrete interface to an external perturbation. The measurement yields a value of a 'polarisation resistance', which can be shown to be inversely related to the rate of corrosion.

There are several problems associated with these techniques. The first is that a secondary (counter) electrode is required to supply the necessary perturbing current to achieve the measurement. A second problem arises from an uncertainty in the size of the area of steel being polarised during the measurement. Additionally the concrete itself is often highly electrically resistive, leading both to difficulties in the application of the external polarisation and to errors in the measurement of the exact value of the 'polarisation resistance' of the interface as the measurement effectively determines the series sum of the concrete and interfacial resistances.

Measurement using existing procedures typically involves the insertion of counter electrode/reference electrode assemblies into the concrete structure at a number of locations, covering these assemblies with fresh concrete or mortar compound and using the above electrochemical techniques to obtain an estimate of the corrosion rate of either the steel reinforcement in the vicinity of the inserted probe or of the probe elements themselves. Such an approach involves considerable and expensive effort in coring the concrete, placing the probes, and making good the concrete surface. Furthermore, the location of the probes is fixed and only a limited number of locations may be monitored at an acceptable cost. The insertion of the probes also leads to a disturbance of the composition of the concrete in the monitoring location, casting significant doubt on the reliability of such measurements. Additionally, the area of steel being polarised is unknown and hence no reliable quantitative estimate of the actual corrosion rate, as opposed to an estimate of a relative rate, may be made. Finally, the probe performance tends to degrade over periods of a few months so that expensive probe renewal is required periodically.

Attempts have been made to overcome these problems In one known system wet material is placed over the surface of the concrete to provide a conductive path. This system suffers from variations in the contact between the electrodes and the concrete surface, is unsuitable for use in hot and dry climates, and can only be applied to essentially horizontal surfaces. In another known system, a 'guard ring' has been employed in an attempt to define the area of reinforcement being polarised. The guard ring system requires an elaborate electrode and electronic arrangement however.

It is an object of the present invention to provide a surface mounting corrosion probe for carrying out corrosion rate meaasurement by any perturbative electrochemical technique such as linear polarisation resistance measurement or a.c. impedance measurement.

According to the present invention, there is provided a surface mounting corrosion probe comprising a frame adapted for securing to a surface of a reinforced concrete structure, and a resilient pad arranged such that when the frame is secured to such a structure one surface of the pad is pressed against the structure surface, wherein a reference electrode is locatable centrally relative to the said one surface so as to contact the surface of any structure against which the pad is pressed, at least an annular portion of the said one surface extending radially outwards from the center towards adjacent the periphery of the pad is electrically conductive, and a terminal is provided which is electrically connected to the said annular portion, whereby corrosion monitoring instruments can be connected to the said terminal and the said reference electrode to monitor corrosion of reinforcement beneath the surface of a structure to which the frame is secured.

The frame may be a simple annular ring defining a peripheral flange engageable by, for example, bolts permanently secured to a concrete structure. The frame can be easily and quickly mounted on the bolts and then removed again as soon as a measurement has been made. A single probe can thus be used to monitor corrosion at a large number of different locations, and can be reliably returned repeatedly to exactly the same locations by relying upon the bolts to accurately locate the probe.

The pad may comprise a sheet of electrically conductive resilient foam. The foam may be retained in the frame by wires extending across the said one surface of the pad. The pad may comprise layers of foam of various rigidities, e.g. a relatively soft front layer with a relatively rigid backing layer.

An aperture may be provided centrally of the pad to enable the insertion of the reference electrode into contact with a surface against which the pad is pressed. Alternatively, the reference electrode could be mounted on the resilient pad.

As the probe can be attached easily to a concrete surface of any orientation for example in the manner described above, and the probe is fixed in position only for the duration of the measurement, which may be as short as one minute in favorable locations, a single probe can cover a large number of locations very economically. Furthermore, the use of the probe does not require any alteration to the monitored structure such as coring or removal of the concrete, but merely the positioning of simple securing devices such as bolts.

An embodiment of the present invention will now be described, by way of example, with reference to the accompanying drawings, in which.

Figure 1:
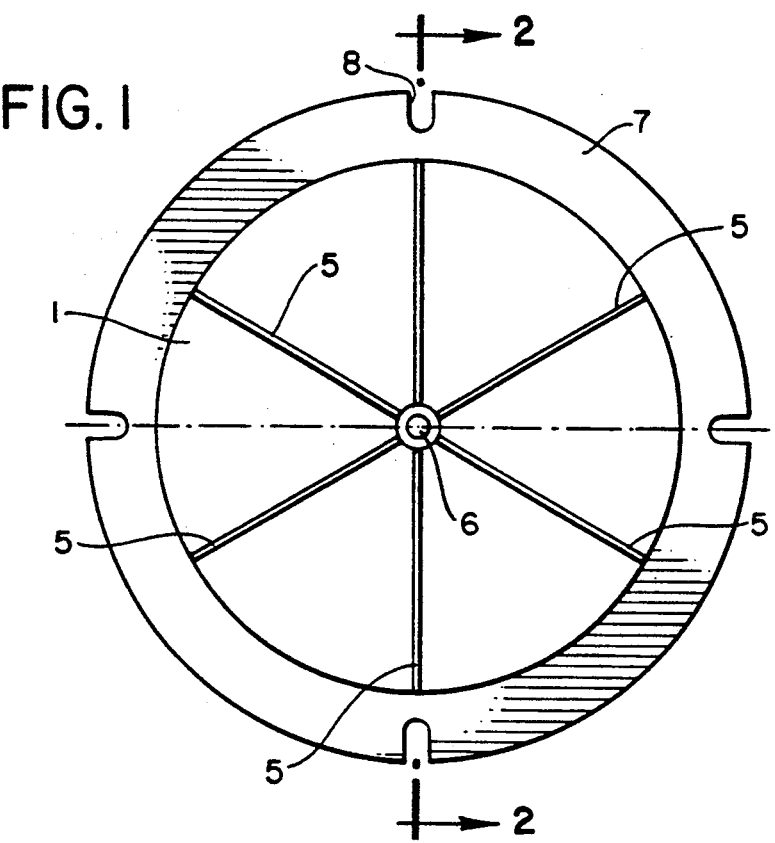
FIG. 1 is a front view of a probe according to the present invention.
Figure 2:
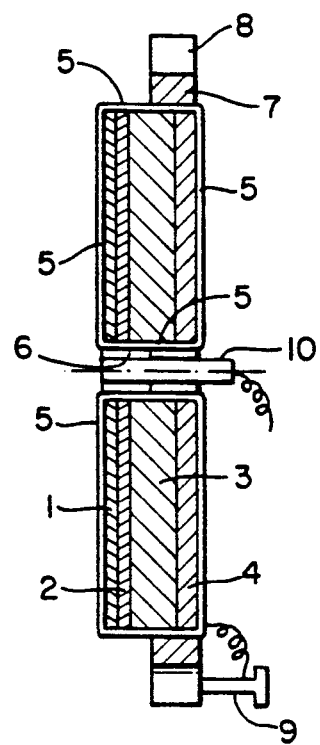
FIG. 2 is a view on section lines 2—2 of FIG. 1.

The illustrated probe comprises a thin disc 1 of flexible soft conductive foam compound of the type commonly used for the storage and protection of static-sensitive electronic devices. The disc 1 is mounted on a disc 2 of rigid conductive foam which is attached to the front face of a disc 3 of compressible non-conductive material such as polyurethane plastic foam compound. This three layer foam pad is in turn attached to the face of a frame in the form of a disc 4 of rigid plastics material, such as polypropylene. The assembly is held together by means of metal wires 5 which pass through holes adjacent the centre of the rigid disc 4, across the front face of the conductive foam disc 1, and back through the rigid disc 4. Alternatively, the wires 5 may be replaced by a flexible metallic mesh placed over the front face of the probe. The retaining wires or mesh also provide an electrical connection to the conductive foam disc 1.

A centrally placed hole 6 in the assembly is used to hold a suitable reference electrode, such as a small Ag-/AgCl reference electrode, which is inserted only for the duration of the measurement. The disc 4 has a peripheral flange 7 defining slots 8 for receiving fixing devices.

In use, the assembly is pressed to the surface of a concrete structure to be monitored by means of fixing devices such as standard metal fasteners, bolts or other clamping arrangements. The fixing devices pass through the slots 8 and are tightened against the flange 7. This results in the compression of the conductive foam discs 1 and 2 and of the non-conductive foam backing 3. The surface of the disc 1 is thus in intimate mechanical contact with the concrete surface, and in good electrical contact with the concrete surface. The reference electrode is then inserted through the central opening 6 so as to contact the concrete surface. The arrangement is then connected electrically to the monitoring device and used as normal for a 'three electrode arrangement', the third electrical connection being made to the steel reinforcement within the structure being monitored at a suitable location.

Several requirements should be fulfilled when using the above-described device. The diameter of the probe should be at least four times the average depth of concrete cover at the monitoring location. The surface of the concrete must be dry and free from any non-conductive surface coating Ideally the probe should be centered over a reinforcing bar cross-over point and its size should be that of the average reinforcing bar spacing in that location, subject to the above size constraint. These limitations are necessary in order to be able to define the area of reinforcement being polarized, which theoretical computer simulations show to be equivalent to the surface of the steel reinforcement present beneath a circle of diameter of approximately 1.2 times that of the probe.

In situations where the shape of the concrete surface precludes the use of a planar probe a suitably shaped probe can be manufactured in most circumstances.

We claim:

1. A surface mounting corrosion probe comprising a frame adapted for securing to a surface of a reinforced concrete structure, and a resilient pad arranged such that when the frame is secured to such a structure one surface of the pad is pressed against the structure surface, wherein a reference electrode is locatable centrally relative to the said one surface so as to contact the surface of any structure against which the pad is pressed, at least an annular portion of the said one surface extending radially outwards from the center towards adjacent the periphery of the pad is electrically conductive, and a terminal is provided which is electrically connected to the said annular portion, whereby corrosion monitoring instruments can be connected to the said terminal and the said reference electrode to monitor corrosion of reinforcement beneath the surface of a structure to which the frame is secured.

2. A corrosion probe according to claim 1, wherein the frame is an annular ring defining a peripheral flange engageable by fixing means permanently secured to a concrete structure.

3. A corrosion probe according to claim 1 wherein the pad comprises a sheet of electrically conductive resilient foam.

4. A corrosion probe according to claim 3, wherein the foam is retained in the frame by wires extending across the said one surface of the pad.

5. A corrosion probe according to claim 3 wherein the pad comprises a relatively soft front layer with a relatively rigid backing layer.

6. A corrosion probe according to claim 1, wherein an aperture is provided centrally of the pad to enable the insertion of the reference electrode into contact with a surface against which the pad is pressed.

7. A corrosion probe according to claim 1 wherein the reference electrode is mounted on the resilient pad.

* * * * *